United States Patent [19]

Minagawa et al.

[11] 4,096,114

[45] Jun. 20, 1978

[54] 2,2,6,6-TETRAMETHYL PIPERIDYL-4-PHOSPHITES AS STABILIZERS FOR ORGANIC POLYMERIC MATERIALS

[75] Inventors: Motonobu Minagawa, Kosigaya; Naohiro Kubota; Toshihiro Shibata, both of Urawa; Kazuo Sugibuchi, Adachi, all of Japan

[73] Assignee: Argus Chemical Corporation, Brooklyn, N.Y.

[21] Appl. No.: 714,940

[22] Filed: Aug. 16, 1976

[30] Foreign Application Priority Data

Aug. 15, 1975 Japan .................................. 50-9929

[51] Int. Cl.² ...................... C07D 211/06; C08K 5/34; C08K 5/35; C08K 5/52
[52] U.S. Cl. .................... 260/45.8 NZ; 260/45.8 NE; 260/293.63; 260/293.64; 544/192
[58] Field of Search ............... 260/45.8 NZ, 45.8 NE, 260/293.63, 293.64, 248 A

[56] References Cited

U.S. PATENT DOCUMENTS 3,975,462   8/1976   Murayama et al. ......... 260/45.8 NE

*Primary Examiner*—Melvyn I. Marquis
*Assistant Examiner*—H. H. Fletcher

[57] ABSTRACT

Organic phosphites are provided having at least one 2,2,6,6-tetramethyl piperidyl substituent attached at the 4-position to phosphorus through oxygen, and at least one polyol or polyphenol group, which are superior light and heat stabilizers for organic polymeric mterials such as polyethylene, polypropylene, polyvinyl chloride, acrylonitrile-butadiene-styrene terpolymers, polyamides, polystyrene, and similar polymers.

30 Claims, No Drawings

2,2,6,6-TETRAMETHYL PIPERIDYL-4-PHOSPHITES AS STABILIZERS FOR ORGANIC POLYMERIC MATERIALS

Hindered 2,2,6,6-tetraalkyl-4-carboxylic acid ester piperidine compounds have been proposed by Murayama et al U.S. Pat. No. 3,640,928 patented Feb. 8, 1972 as light and heat stabilizers for synthetic polymers, such as polyolefins, polyvinyl chloride, polyvinylidene chloride, polyurethanes, and polyamides. These compounds have the general formula:

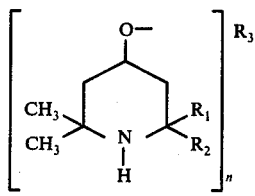

or a salt thereof.

In the above Formula:

$R_1$ and $R_2$ which may be the same or different, each are an alkyl group such as methyl, ethyl, isopropyl or dodecyl, or they form, together with the carbon atom to which they are attached, a saturated alicyclic group such as:

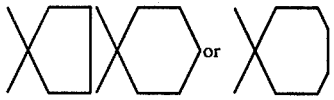

or a group of the formula

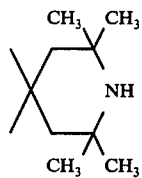

n is an integer of 1 to 3 inclusive: and
$R_3$ is an acyl group.

These compounds have proved to be particularly acceptable because they do not impart a discoloration of their own to the synthetic polymer. The compounds generally employed previously have either been highly colored, such as the nickel compounds (which are normally green) and the 2-hydroxybenzophenones (which are varying shades and intensities of yellow). They also show very little tendency towards sublimation and exudation, and they have an excellent stabilizing action against both heat and light deterioration.

Consequently, the Murayama et al patent has been followed by a large number of patent and literature disclosures by Murayama et al and others of compounds including a 2,2,6,6-tetrasubstituted-4-piperidyl group attached to a base molecule of varying structures.

Murayama et al U.S. Pat. No. 3,898,303 patented Aug. 5, 1975 propose piperidino-spiro-hydantoin derivatives having the formula:

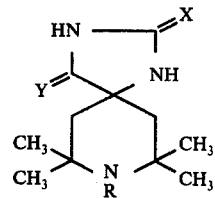

wherein

R represents an alkyl group, an alkenyl group, an alkenoyl group which may be substituted with an aryl group, a hydroxyalkyl group, an alkoxyalkyl group, an alkoxycarbonylalkyl group, an acyloxyalkyl group, a cyanoalkyl group or nitroso group, and X and Y individually represent oxygen atom or sulfur atom.

Murayama et al in U.S. Pat. No. 3,899,464 patented Aug. 12, 1975 disclose a variation of the piperidino spiro compounds having the formula:

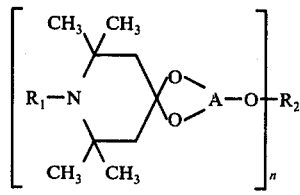

wherein $R_1$ represents hydrogen atom, an alkyl group, a substituted alkyl group, an alkenyl group, an alkynyl group, a substituted or unsubstituted aralkyl group, an aliphatic acyl group, an alkoxycarbonyl group or an aralkoxycarbonyl group, n is an integer of 1 to 4;

wherein n is 1, $R_2$ represents hydrogen atom, an aliphatic, aromatic or heterocyclic monoacyl group, an alkyl group, an alkenyl group, an alkynyl group, an aralkyl group, an aryl group, an alkoxyalkyl group, an epoxyalkyl group, an alkoxysulfonylalkyl group, N-substituted carbamoyl group, a N-substituted thiocarbamoyl group, a monovalent group from an oxoacid or group

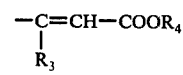

in which $R_3$ represents hydrogen atom, a lower alkyl group or phenyl group and $R_4$ represents an alkyl group;

when n is 2, $R_2$ represents carbonyl group, an aliphatic or aromatic diacyl group, an alkylene group, an alkenylene group, an alkynylene group, an aralkylene group, a N-substituted dicarbamoyl group or a divalent group from an oxoacid;

when n is 3, $R_2$ represents an aromatic triacyl group or a trivalent group from an oxoacid; and when n is 4, $R_2$ represents an aromatic tetraacyl group, and A represents a group

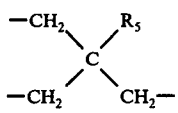

in which
R₅ represents hydrogen atom or a lower alkyl group or, when $n$ is 1, $R_5$ may represent together with $R_2$ a group

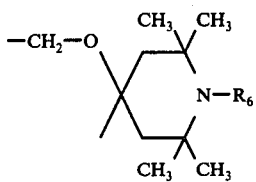

in which
$R_6$ represents the same group as defined in $R_1$ and may be the same or different from $R_1$, or a group

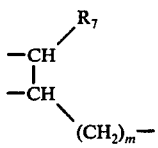

in which
$m$ is 1 or 2 and $R_7$ represents hydrogen atom or, when $n$ and $m$ are 1, $R_7$ represents methylene group together with $R_2$.

Murayama et al U.S. Pat. No. 3,933,735 patented Jan. 20, 1976 propose 4-piperidone derivatives having a structure similar to the 4-piperidyl derivatives, but with a keto oxygen at the 4-position of the piperidine ring.

Murayama et al U.S. Pat. No. 3,941,744 patented Mar. 2, 1976, disclose another variation of the piperidino spiro derivatives having the formula:

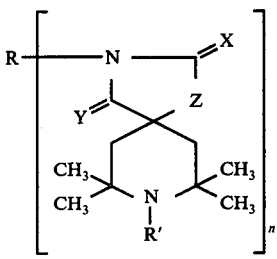

wherein
R' represents an alkyl group, a substituted alkyl group, an acyl group, an alkoxycarbonyl group, a substituted alkoxycarbonyl group, an amino group, a substituted amino group or nitroso group;
X represents oxygen atom or sulfur atom;
Y represents oxygen atom, sulfur atom or a group of the formula =N—R" in which R" is hydrogen atom, an alkyl group or a substituted alkyl group;
Z represents oxygen atom or a group of the formula >N—R'" is hydrogen atom, an alkyl group or a substituted alkyl group;
$n$ is an integer of 1 through 4 inclusive; and
R represents, when $n$ is 1, an alkyl group, a substituted alkyl group, an aryl group, a substituted aryl group, a cycloalkyl group, an alkoxycarbonyl group, a substituted alkoxycarbonyl group, a substituted phosphino group or a substituted phosphinyl group, when $n$ is 2, an alkylene group, an alkenylene group, an arylene group, a substituted arylene group, an aralkylene group, an alkylenediphenylene group, a bis-(acyloxyalkylene) group, an alkylene-bis-(oxycarbonylalkyl)group, a dialkylene ether group or a diphenylene ether group, when $n$ is 3, an alkanetriyl group, a tris-(acyloxyalkylene)- group, an alkane-tris-(oxycarbonylalkyl)group or a group of the group

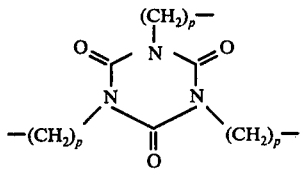

in which
$p$ is an integer of 1 through 8 inclusive, and when $n$ is 4, an alkane tetrayl group, a tetrakis-(acyloxyalkylene) group or an alkanetetrakis-(oxycarbonylalkyl) group.

Murayama et al U.S. Pat. No. 3,940,363 patented Feb. 24, 1976 disclose a further variation in which two 2,2,6,6-tetrasubstituted-4-piperidyl groups are linked together via the ring nitrogen atom to an R' alkylene linking group, which may be interrupted with an oxygen or sulfur atom, an alkenylene group, an alkynylene group, an aralkylene group, an aliphatic diacyl group, a group having the formula:

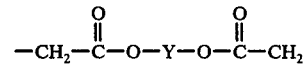

in which
$n$ is an integer of 1 or 2 and X is an alkylene group, or o-, m- or p-phenylene group or the carbon atoms of CO groups may be directly joined in the absence of X or a group of the formula:

$$-CH_2-\overset{O}{\underset{\|}{C}}-O-Y-O-\overset{O}{\underset{\|}{C}}-CH_2$$

in which
Y is an alkylene group or o-, m- or p-phenylene group.

Ramey et al U.S. Pat. Nos. 3,899,491, patented Aug. 12, 1975 and 3,920,659, patented Nov. 18, 1975, disclose alkyl alkanoate derivatives of substituted piperazines and substituted piperazinodiones. The substituted piperazines of U.S. Pat. No. 3,899,491 have the formula:

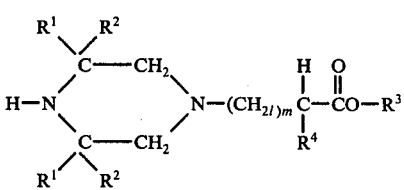

wherein

R[1] and R[2] are methyl or together with the carbon to which they are bound form a mono-cyclic ring system having 5 or 6 carbon atoms;
R[3] is an alkyl group of from one to twenty atoms;
R[4] is hydrogen or methyl, and
m is 0 or 1.

The substituted piperazinodiones of No. 3,920,659 have the formula:

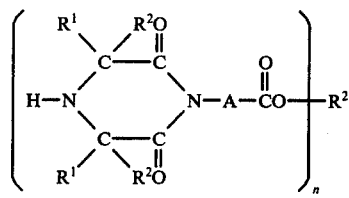

wherein
R[1] and R[2] are independently of each other methyl or ethyl or together with the carbon to which they are bound form a cyclopentyl or cyclohexyl ring, which is unsubstituted or substituted with a methyl group;
n is an integer of from 1 to 2;
when n is 1, R[3] is an alkyl group of from one to twenty carbon atoms;
when n is 2, R[3] is an alkylene group of from two to eight carbon atoms; and
A is a straight or branched chain (lower) alkylene group containing from one to six carbon atoms with the limitation that the terminals of said alkylene group bear only hydrogen or one (lower) alkyl group.

Ramey et al U.S. Pat. No. 3,920,661 patented Nov. 18, 1975 disclose dicarboxylic acids and salts in which one carboxylic acid group is esterified with a 2,2,6,6-tetrasubstituted-4-hydroxy piperidine and having the formula:

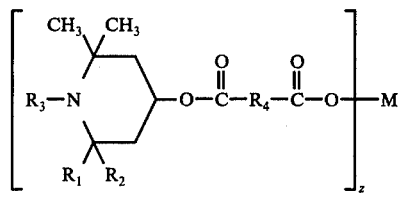

wherein
R[1] and R[2] independently of each other are straight- or branched-chain alkyl having from one to six carbon atoms, or together with the carbon to which they are bound form a cyclopentyl or cyclohexyl ring, which is unsubstituted or substituted with a methyl group;
R[3] is hydrogen, alkyl having one to twelve carbon atoms, β-methoxyethyl, alkenyl having three or four carbon atoms, propargyl, benzyl or alkyl-substituted benzyl;
R[4] is straight or branched-chain alkylene having five to eight carbon atoms, or the group $(CH_2)_mY(CH_2)_n$ wherein Y is oxygen or sulfur and m and n independently of each other are an integer from 1 to 3;
M is hydrogen or a metal selected from the group consisting of barium, nickel, manganese, calcium, zinc, iron, sodium, cobalt, tin, and dialkyl tin, and z has a value of from 1 to 4, the value of z being the same as the available valence of M.

Ramey et al. U.S. Pat. No. 3,939,163 patented Feb. 17, 1976 disclose closely similar compounds in which R[4] is alkylene having from one to four carbon atoms.

Randell et al U.S. Pat. No. 3,939,170 patented Feb. 17, 1976 disclose dehydropyridinyl sulphides, sulphoxides and sulphones having the formula:

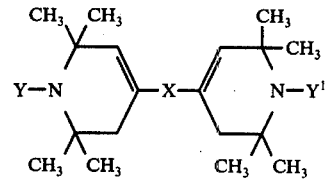

wherein
X is S, SO or $SO_2$ and Y and Y[1] are the same or different and each is H, OH, O- or a straight- or branched alkyl residue having from one to four carbon atoms, and salts thereof when Y and Y[1] are other than O-

Randell et al in published U.S. Pat. application Ser. No. B408,123 published Apr. 13, 1976 disclose substituted piperidine-4-ols having the formula:

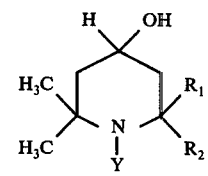

wherein
R[1] and R[2] are the same or different and each is a straight- or branched alkyl residue having from one to twelve carbon atoms, or R[1] and R[2], together with the carbon atom to which they are attached, form a cycloalkyl residue having from five to twelve carbon atoms or the group:

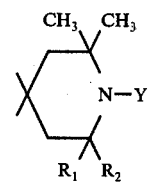

wherein
R[1] and R[2] have their previous significance and Y is a straight- or branched alkyl residue having from one to twenty carbon atoms, an alkenyl or alkynyl residue having from three to twenty carbon atoms, an aralkyl residue having from seven to twelve carbon atoms or the group —$CH_2X$ wherein X is the group

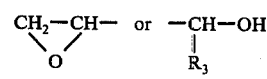

wherein
R[3] is hydrogen, a methyl or phenyl residue, the group

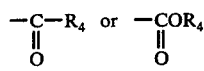

wherein

R₄ is an alkyl residue having from one to twenty carbon atoms.

Cook U.S. Pat. No. 3,929,804 patented Dec. 30, 1975 discloses 4-piperidine acetamide compounds having the formula

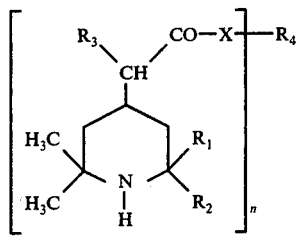

wherein $R_1$ and $R_2$ are the same or different and each is a straight- or branched alkyl residue having from 1 to 12 carbon atoms, or $R_1$ and $R_2$, together with the carbon atom to which they are attached form a cycloalkyl group having from five to twelve carbon atoms;

$R_3$ is hydrogen, a straight- or branched alkyl residue having from one to four carbon atoms, an aralkyl residue having from 7 to 9 carbon atoms or a cycloalkyl group having from five or six carbon atoms;

$R_4$ is a metal ion or a hydrocarbyl residue having from 2 to 20 carbon atoms and being either unsubstituted or substituted by halogen or interrupted by one or more oxygen or sulphur atoms;

X is —O—, —S—, or $>NR_5$, wherein $R_5$ has the same significance as $R_3$; and n is 2, 3 or 4; as well as salts of the amine function of the compounds of formula I.

Cook U.S. Pat. No. 3,939,168 patented Feb. 17, 1976 discloses closely similar compounds having a Y substituent on the piperidyl nitrogen atom, Y being alkyl, alkenyl, aralkyl or a group

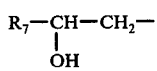

wherein $R_7$ is hydrogen, alkyl or phenyl.

In accordance with the instant invention, 2,2,6,6-tetramethylpiperidyl-4-phosphites are provided having the formula:

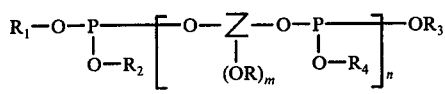

$R_1$ is selected from the group consisting of:

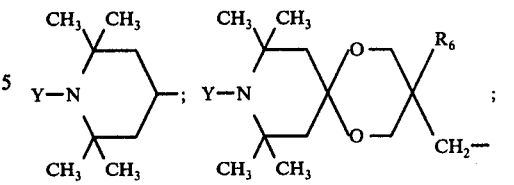

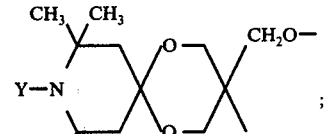

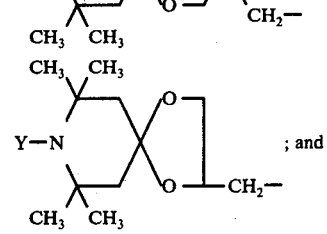

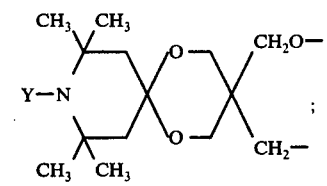

$R_2$, $R_3$ and $R_4$ (and $R_5$ in Formula IV below) are selected from the group consisting of:

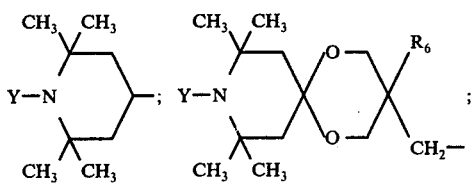

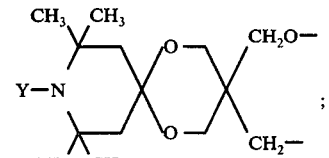

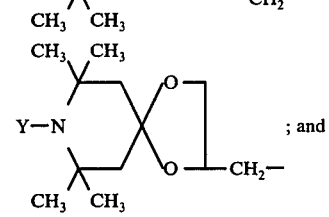

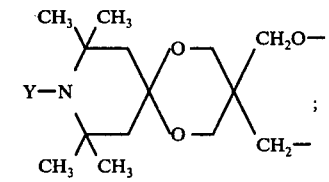

hydrogen, alkyl having from one to about twenty carbon atoms; aryl and hydroxyaryl having from 6 to about 20 carbon atoms; alkyl aryl and aryl alkyl having from 7 to about 20 carbon atoms; hydroxyalkyl and hydroxyalkylene oxyalkylene having from 2 to about 30 carbon atoms; and $R_1$ and $R_2$; taken together to form

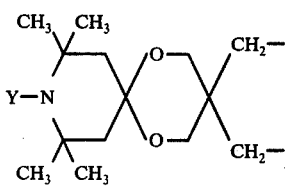

R is selected from the group consisting of hydrogen and

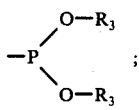

$R_6$ is alkyl having from one to about six carbon atoms;
Y is selected from the group consisting of hydrogen and oxygen;
m is a number selected from 0, 1, 2, 3 and 4;
n is a number selected from zero to 20, when n is zero, at least one of $R_2$ and $R_3$ being derived from a polyol or a polyphenol.
Z is selected from the group consisting of bivalent, trivalent and tetravalent alkylene having from 2 to about 30 carbon atoms; bivalent, trivalent and tetravalent arylene, bis arylene and tris arylene, having from 6 to about 30 carbon atoms; mono, di or tri N-substituted cyanuric acid; and taken with OR, $R_1$ or $R_2$ and $R_3$ or $R_4$ to form the group:

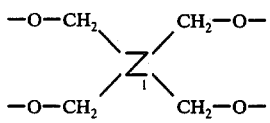

in which $Z_1$ is selected from the group consisting of

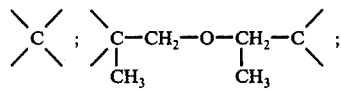

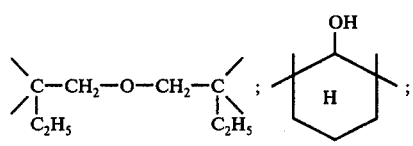

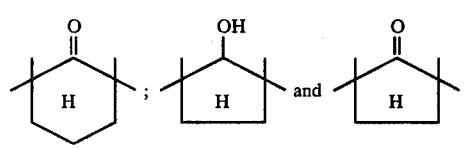

In the case where the Z substituent is alkylene, the Z radical is a polyol residue, and the compounds take the form:

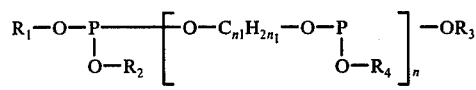

where:
$n_1$ is a number from 2 to 20; and
$R_1$, $R_2$, $R_3$, and n are as in Formula I.

When Z is arylene, the radical is polyphenol residue, and the compounds take the form:

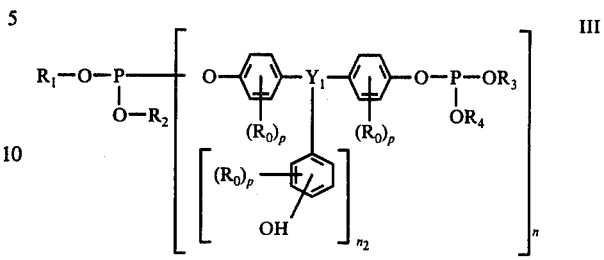

where:
$R_0$ is alkyl having from one to about twenty carbon atoms;
p is a number selected from zero to 4;
$n_2$ is zero or 1; and
$Y_1$ is a bivalent or trivalent linking radical and is selected from the group consisting of alkylene groups having from one to about twenty carbon atoms; oxygen; sulfur; cycloalkylene having from about five to about seven atoms; and arylene having from six to about thirty atoms.
$R_0$ and OH can be in any position or positions of the ring. OH is preferably in the para position to $Y_1$.

When Z is taken together with OR, R, or $R_2$ and $R_3$ or $R_4$, the compounds take the form:

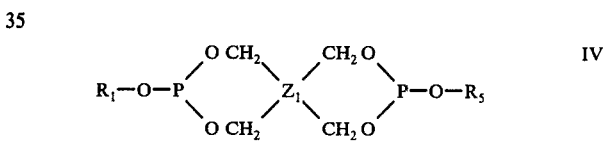

where $R_1$, $R_5$ and $Z_1$ are as above.

Other variations will be apparent from consideration of Formula I.

The $R_0$, $R_2$, $R_3$, $R_4$, $R_5$ and $R_6$ alkyl have from one to about twenty carbon atoms. Exemplary are methyl, ethyl, n-propyl, isopropyl, n-butyl, isobutyl, tertiary butyl, secondary butyl, n-amyl, isoamyl, tertiary amyl, n-hexyl, isohexyl, secondary hexyl; tertiary hexyl; n-heptyl; isoheptyl; n-octyl; isooctyl; n-nonyl, n-isononyl, t-nonyl; decyl; undecyl; dodecyl; tridecyl; tetradecyl, hexadecyl, octadecyl, and eicosyl.

The $R_2$, $R_3$, $R_4$ and $R_5$ aryl have from six to twenty carbon atoms and include phenyl, napthyl and phenanthryl.

The $R_2$, $R_3$, $R_4$ and $R_5$ aralkyl have from seven to about twenty carbon atoms, and include phenmethyl, phenethyl, phenpropyl, phenbutyl, phendecyl, phendodecyl, and naphthethyl, methyl phenyl, dimethyl phenyl, trimethyl phenyl, octyl phenyl, ethyl butyl phenyl, and ethyl phenyl dodecyl phenyl.

The $R_2$ or $R_3$ or $R_4$ or $R_5$ hydroxy aryl can take the form:

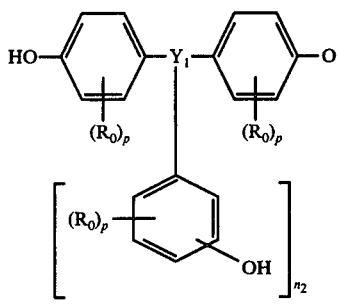

where $Y_1$, $R_0$, $n_2$ and p are as in Formula III.

Exemplary Y groups are alkylene, alkylidene, and alkenylene; arylene, alkylarylene, arylalkylene; cycbalkylene, cycloalkylidene, and oxa- and thia-substituted such groups; carbonyl groups, tetrahydrofuranes, esters and triazino groups, The Y groups are usually bi, tri, or tetravalent, connecting two, three or four

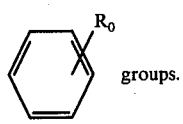

However, higher valence Y groups, connecting more than four

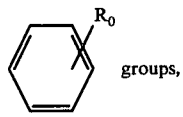

can also be used. According to their constitution, the Y groups can be assigned to subgenera as follows:

(1) Y groups where at least one carbon in a chain or cyclic arrangement connect the aromatic groups, such as

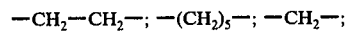
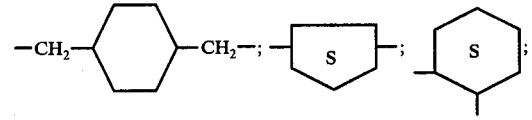
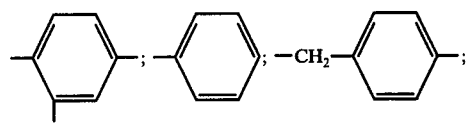
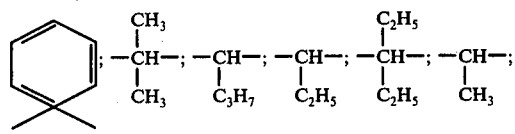
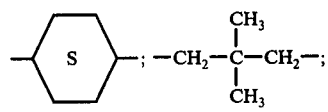
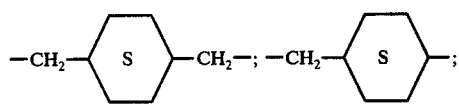

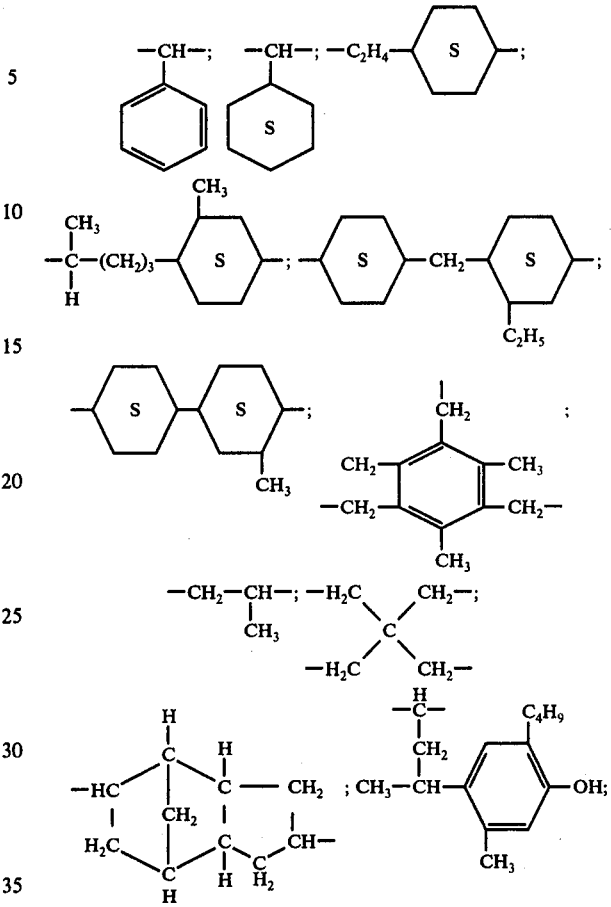

(2) Y groups where only atoms other than carbon link the aromatic rings, such as

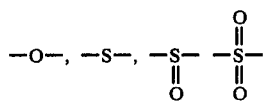

and —(S)x— where X is a number from one to 10;

(3) Y groups made up of more than a single atom including both carbon and other atoms linking the aromatic nuclei, such as

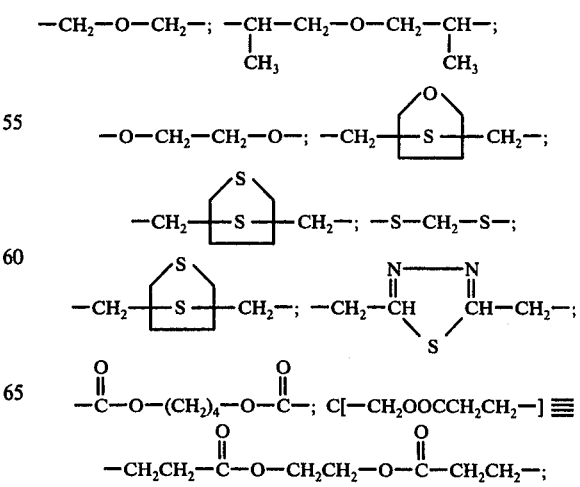

-continued
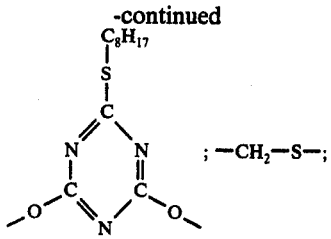 ; —CH₂—S—;
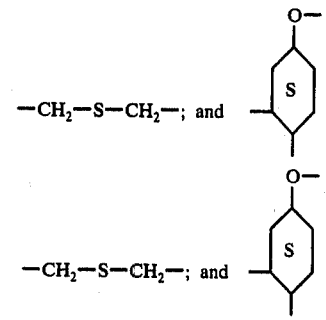 —CH₂—S—CH₂—; and
—CH₂—S—CH₂—; and
The following compounds are exemplary:[1]
No. 1
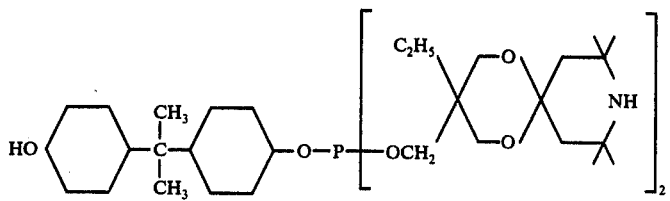
No. 2
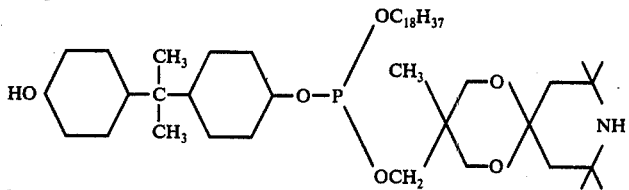
No. 3
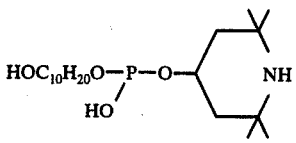
No. 4
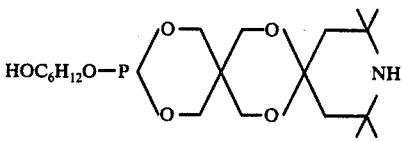
No. 5
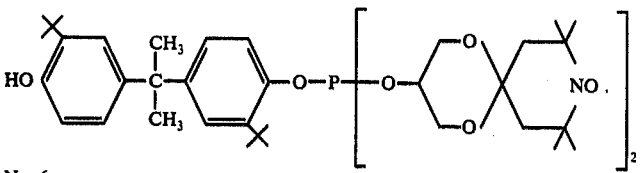
No. 6
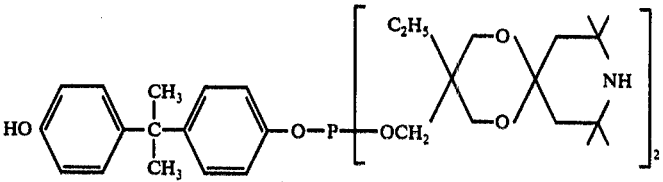
No. 7
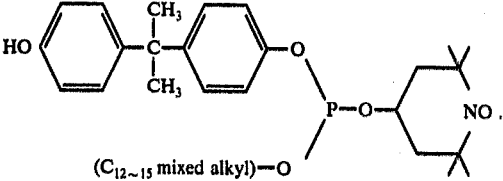

-continued
No. 8
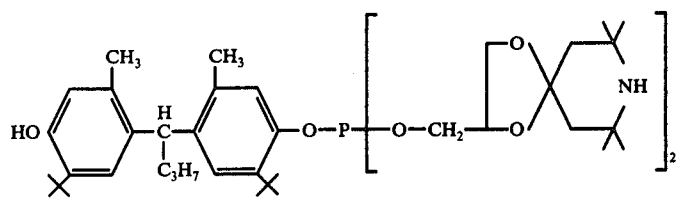
No. 9
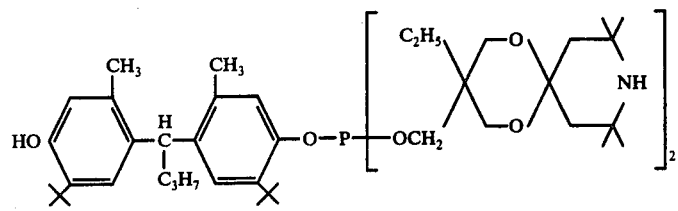
No. 10
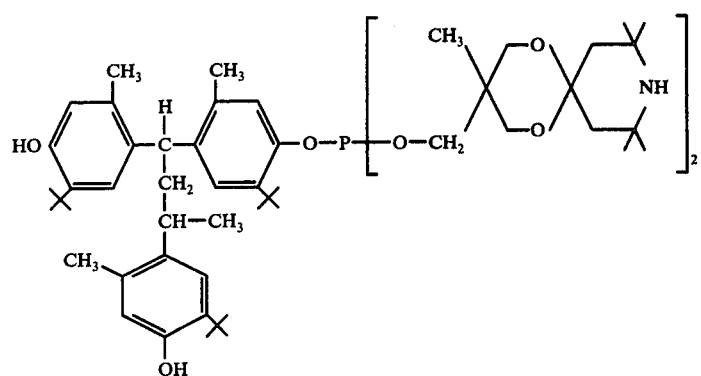
No. 11
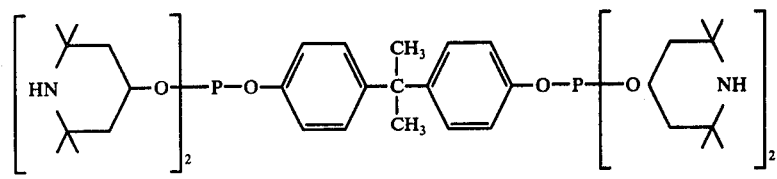
No. 12
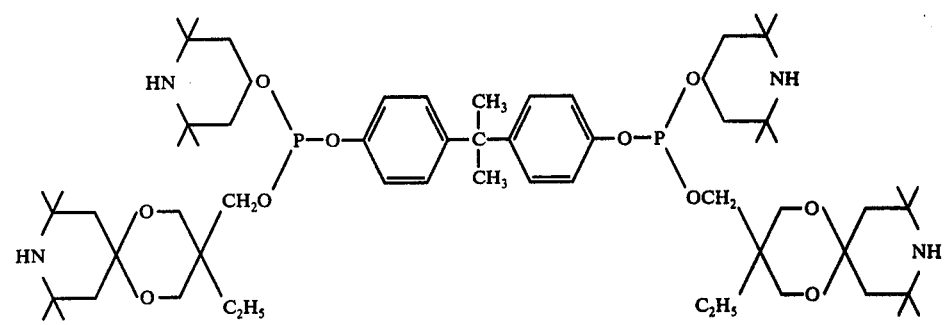
No. 13
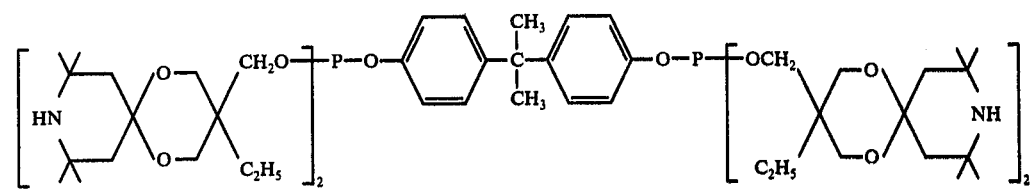
No. 14

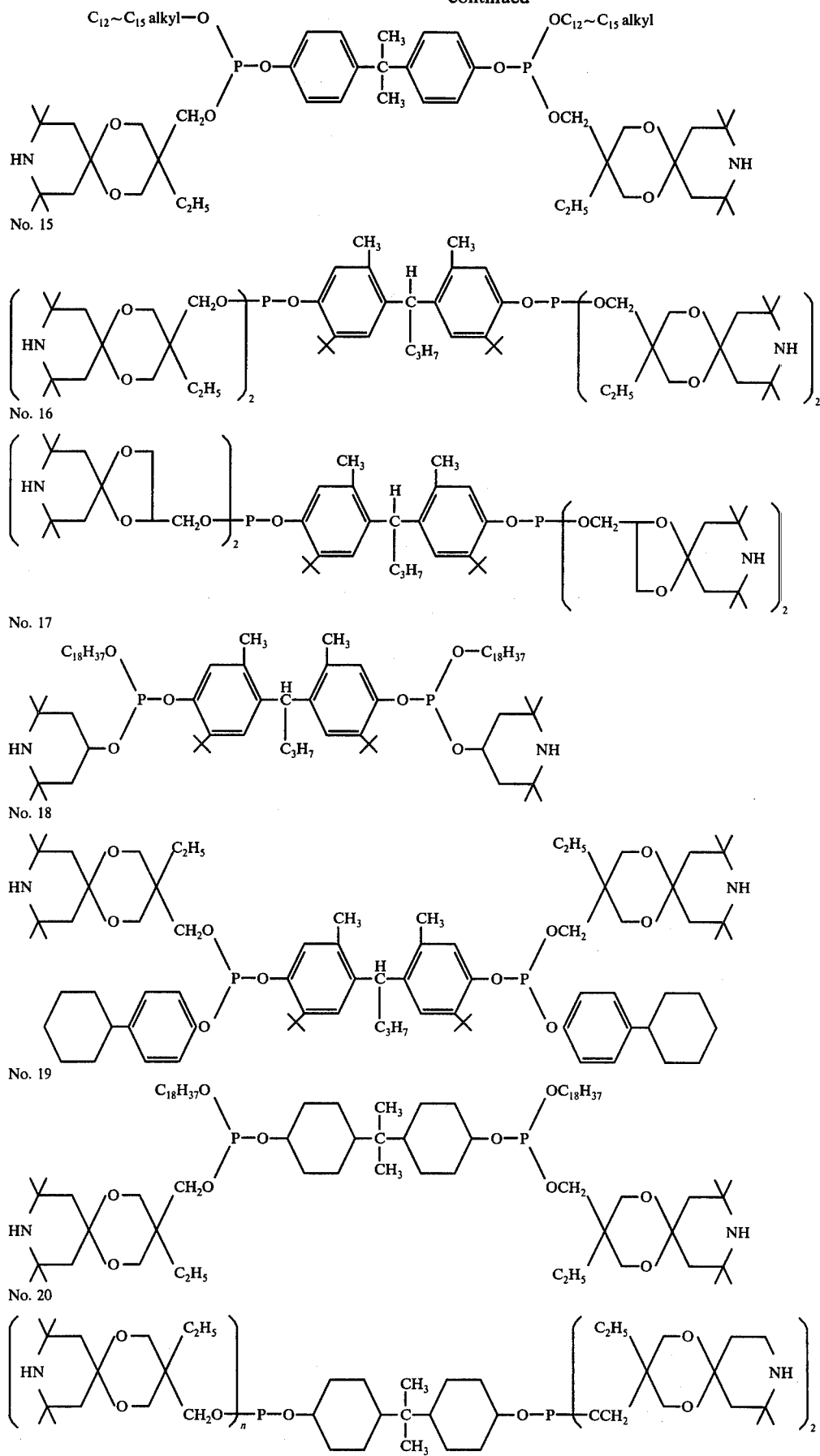

-continued
No. 21
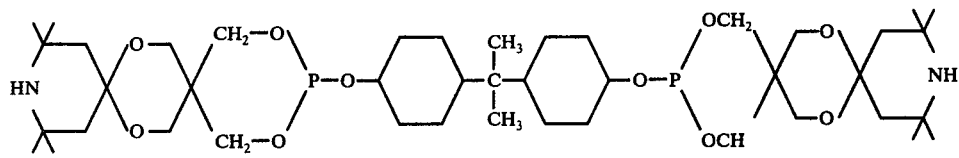
No. 22
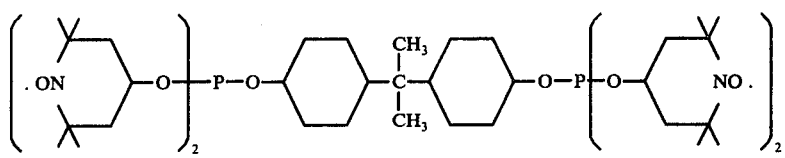
No. 23
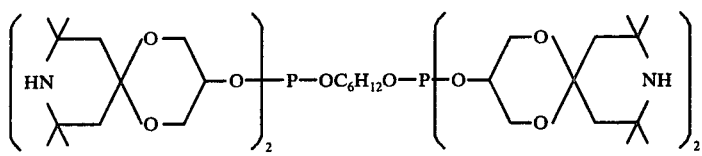
No. 24
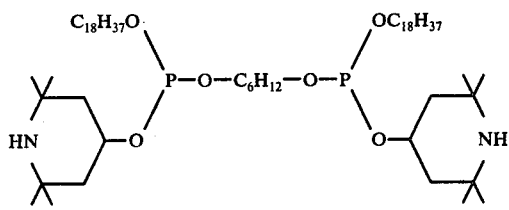
No. 25
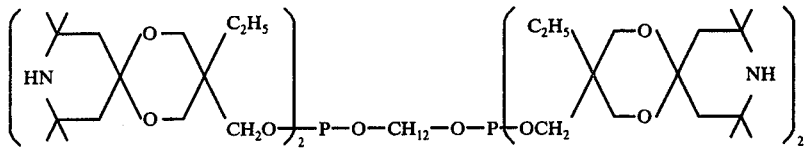
No. 26
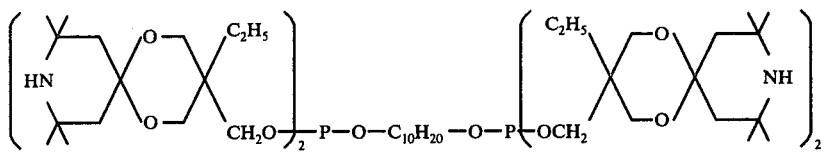
No. 27
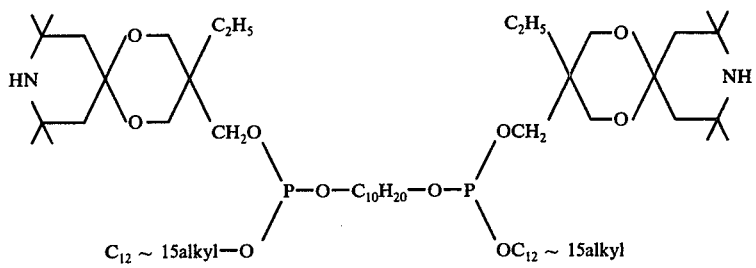
No. 28
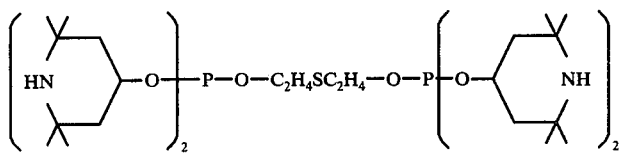
No. 29

-continued
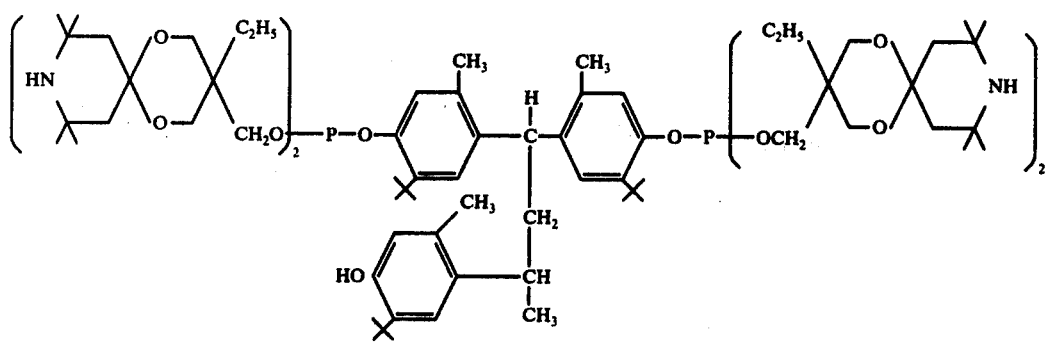
No. 30
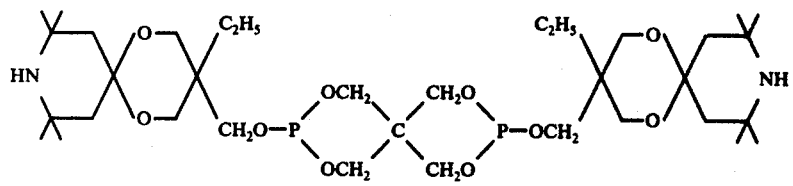
No. 31
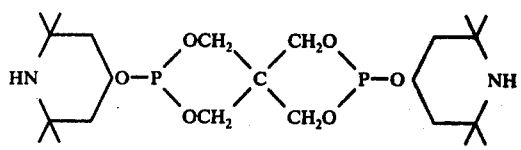
No. 32
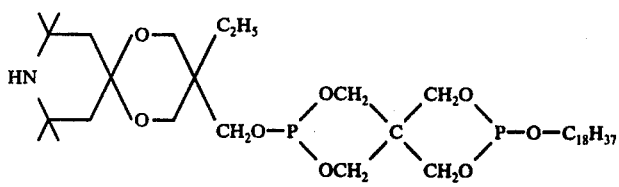
No. 33
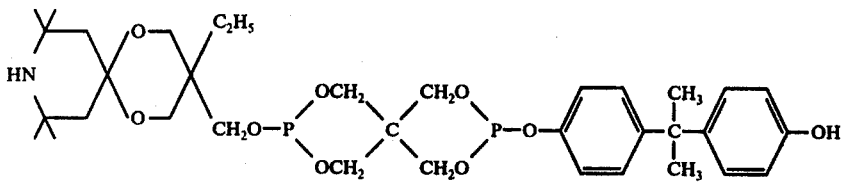
No. 34
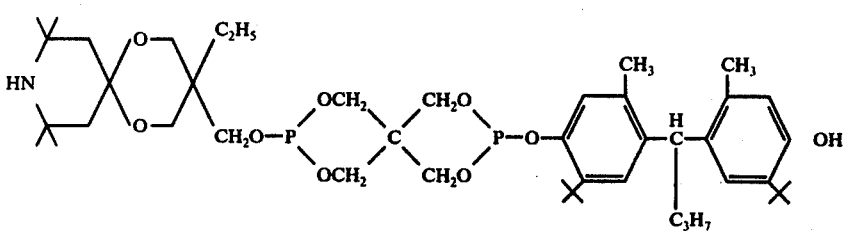
No. 35
No. 36

-continued
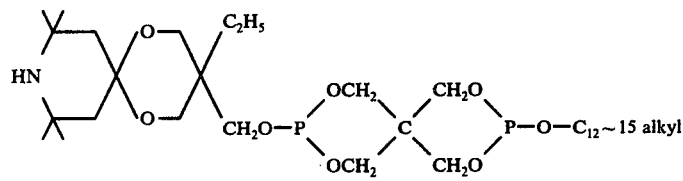
No. 37
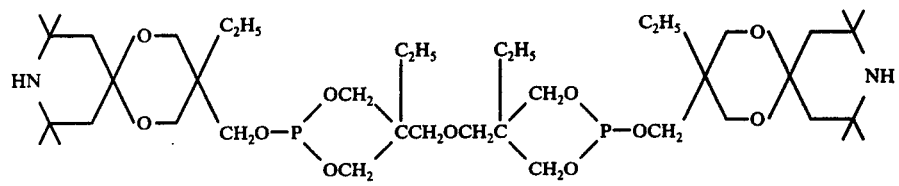
No. 38
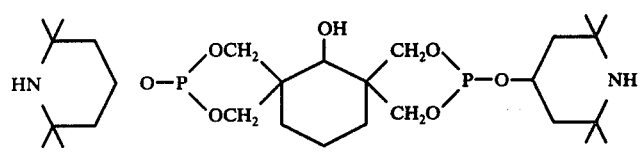
No. 39
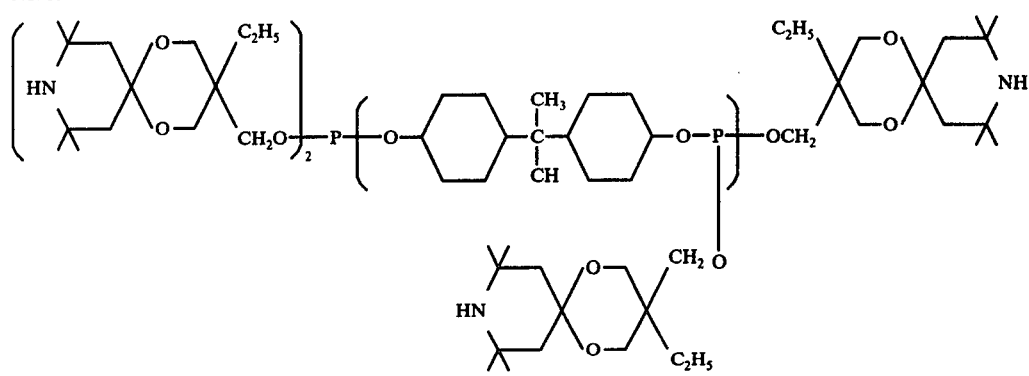
No. 40
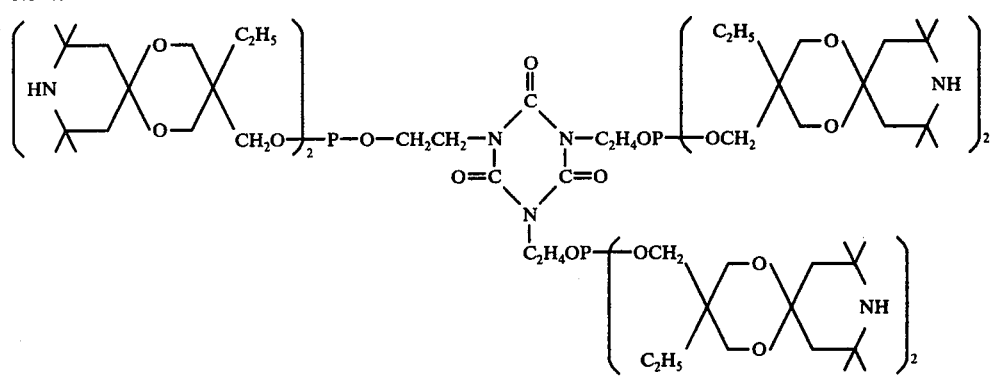
No. 41
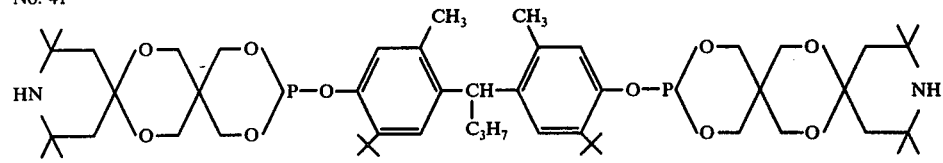
No. 42
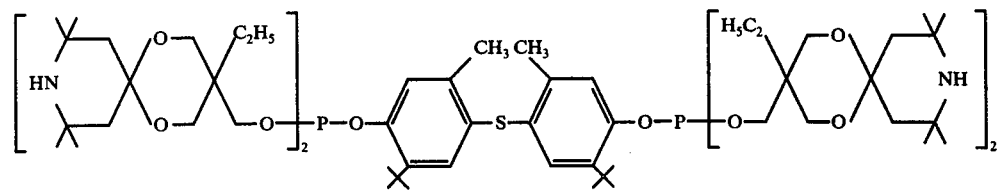
No. 43

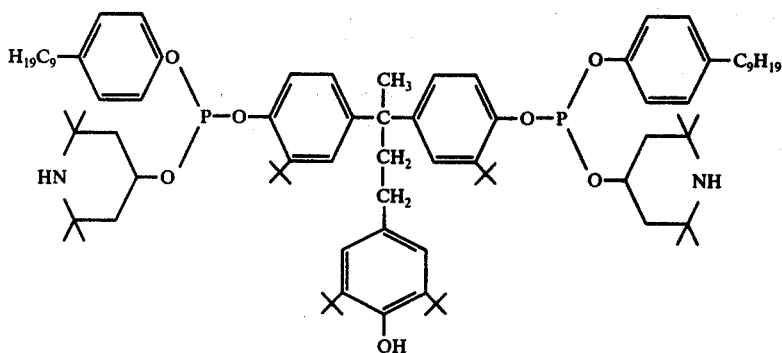

No. 44

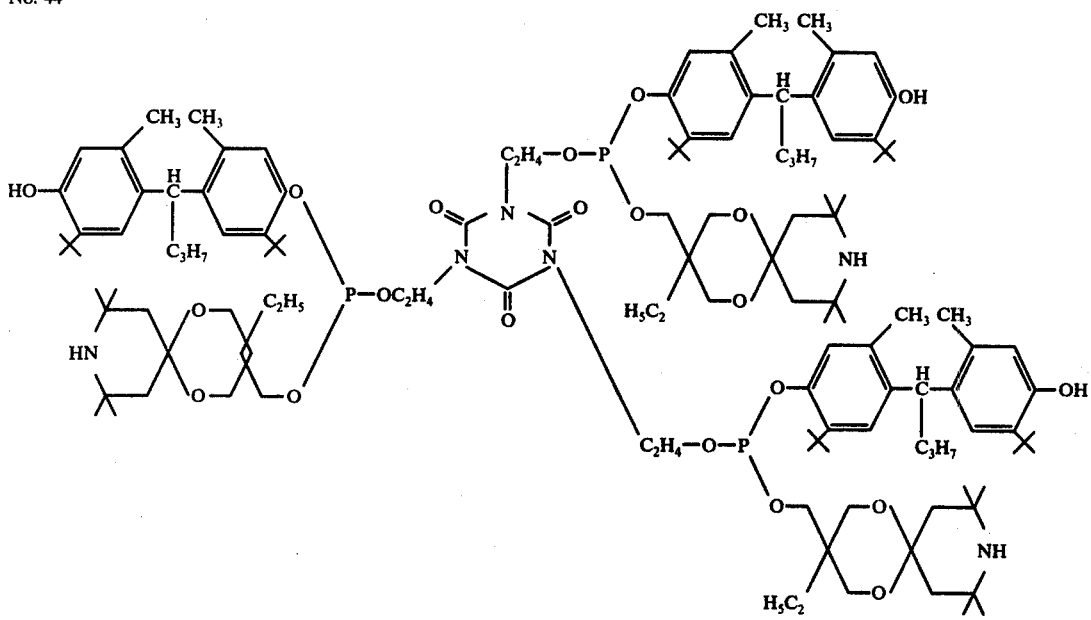

No. 6

These compounds are readily prepared by conventional transesterification reaction procedures, starting from a simple triphosphite such as triphenylphosphite or trimethyl phosphite and the corresponding polyol, polyphenol, or derivative thereof. Transesterification or organic triphosphites is normally carried out in the presence of an acid or base serving as a catalyst, and the phenol or alcohol liberated in the course of the transesterification is removed by distillation, so as to drive the reaction forward. Thus, the starting triphosphite should be one in which the phenol or alcohol liberated in the course of the transesterification has a lower boiling point at normal or subatmospheric pressure than the alcohol or phenol to be introduced by the transesterification reaction.

The following Examples are illustrative of the preparatory procedure.

EXAMPLE I

Bisphenol A, 2,2-dimethyl-methylene-bis-phenol, 0.1 mol, 22.8 grams, triphenyl phosphite, 31 grams, 0.1 mol; 9-aza-3-ethyl-3-hydroxymethyl-8,8,10,10-tetramethyl-1,5-dioxaspyro (5.5) undecane, 54.2 g (0.2 mol); and potassium carbonate, 0.1 g, were mixed and reacted under reflux at 130° C for three hours under a nitrogen gas atmosphere. Distillation of phenol then was begun, and continued at 160° C for two hours under reduced pressure. A colorless sticky liquid was obtained, having a phosphorus content of 3.60%, corresponding to the calculated value of 3.63% for the compound of the formula

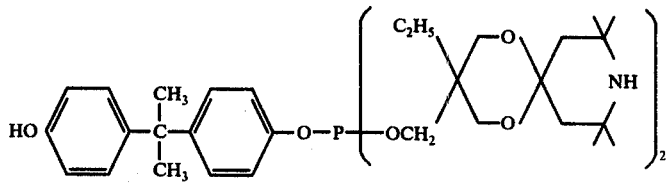

EXAMPLE II

Triphenyl phosphite 31 grams (0.1 mol), Bisphenol A 2,2-dimethyl-methylene-bis-phenol, 11.4 grams, (0.05 mol); 9-aza-3-ethyl-3-hydroxymethyl-8,8,10,10-tetramethyl-1,5-dioxaspyrao-(5,5) undecane (0.2 mol) 54.2 grams; and potassium carbonate 0.1 gram were mixed and reacted under reflux at 140° C for three hours under a nitrogen gas atmosphere. Distillation of phenol at 170° C was then begun, under reduced pressure, and continued for 2 hours. The reaction product was a white glassy solid whose melting point was 47°–55° C. The phosphorus content was 3.25%, corresponding to the calculated phosphorus content of 3.20% for the compound of the formula:

No. 13

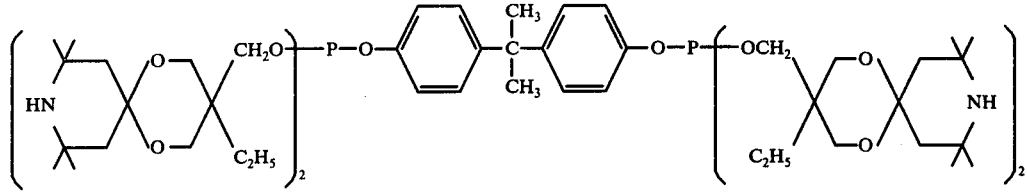

EXAMPLE III

Trimethyl phosphite 12.4 g (0.1 mol), pentaerythritol 6.8 g (0.05 mol), 9-aza-3-hydroxymethyl-8,8,10,10-tetramethyl-1,5-dioxaspyro (5.5) undecane 27.1 g (0.1 mol) and potassium carbonate 0.05 g were mixed and heated under reflux at 110° C while methanol was distilled off. After all of the methanol calculated to be liberated had been distilled, the reaction temperature was brought up to 160° C, and held there for one hour. The reaction product was a glassy solid, melting point 43°–59° C. The phosphorus content was 6.64%, corresponding to the calculated value of 6.70% for the compound of the formula:

No. 31

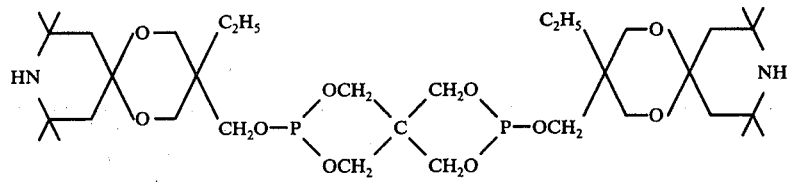

The 2,2,6,6-tetramethyl-piperidyl-4-phosphites of the invention are effective stabilizers to enhance the resistance to deterioration due to heat and/or light of synthetic polymeric materials which are susceptible to such degradation, including polyolefins such as low density polyethylene, high density polyethylene, polypropylene, polybutylene, polyisobutylene, polypentylene, and polyisopentylene; polystyrene; polydienes, such as polybutadiene and polyisoprene; and copolymers of olefins and dienes with other ethylenically and acetylenically unsaturated monomers, such as ethylene-propylene copolymers, ethylene-butene copolymers, ethylenepentane copolymers, ethylene-vinyl acetate copolymers, styrene-butadiene copolymers, acrylonitrile-styrene-butadiene copolymers, synthetic rubbers of all types, such as polychloroprene; polyvinyl halides, including polyvinyl chloride homopolymer, polyvinylidene chloride, and copolymers of vinyl chloride and vinylidene chloride; vinyl chloride and vinyl acetate; vinylidene chloride and vinyl acetate; and other ethylenically unsaturated monomers; polyacetals such as polyoxymethylene and polyoxyethylene; polyesters such as polyethylene glycol-terephthalic acid ester polymers; polyamides such as polyepsiloncaprolactam; polyhexamethylene adipamide and polydecamethylene adipamide; polyurethanes; and epoxy resins.

The synthetic polymer can be in any physical form, including (for example) filaments, yarns, films, sheets, molded articles, latex, and foam.

The stabilizers of the invention can be employed as the sole stabilizer, or, preferably, in combination with other conventional heat and light stabilizers for the particular synthetic polymer.

Thus, for example, in the case of polyvinyl chloride resins, other polyvinyl chloride resin heat stabilizers can be included, including polyvalent metal fatty acid salts such as barium and cadmium salts of the higher fatty acids; organic triphosphites; organotin compounds; hindered phenols; and epoxy compounds.

With polyolefin resins there can be employed fatty acid salts of polyvalent metals, organic phosphites, phenolic antioxidants, and the higher fatty acid esters of thiodipropionic acids, such as, for example, dilauryl thiodipropionate.

With polyamide resin compositions, polyamide stabilizers such as copper salts in combination with iodides and/or phosphorus compounds and salts of divalent manganese can be used.

With synthetic rubbers and acrylonitrile butadiene styrene terpolymers, antioxidants such as hindered phenols and bis-phenols, polyvalent metal salts of the higher fatty acids, and organic phosphites can be used.

In addition, other conventional additives for synthetic polymers, such as plasticizers, lubricants, emulsifiers, antistatic agents, flame proofing agents, pigments and fillers, can be employed.

The following Examples in the opinion of the inventors represent preferred embodiments of synthetic resin compositions in accordance with the invention.

EXAMPLES 1 to 7

A group of six polyvinyl chloride resin compositions was prepared having the following formulation:

| Ingredient | Parts by Weight |
|---|---|
| Polyvinyl chloride | 100 |
| Dioctylphthalate | 50 |
| Epoxidized soya bean oil | 2.0 |
| Ca stearate | 1.0 |
| Zn stearate | 0.1 |

-continued

| Ingredient | Parts by Weight |
|---|---|
| Stabilizer as shown in Table I | 0.1 |

This formulation was blended and sheeted off on a two roll mill to form sheets 1 mm thick. The light resistance of these sheets was then determined by placing strips 1 cm long in a Weather-O-Meter, and exposing them to ultraviolet light. The time in hours was then noted (reported in Table I as hours to failure) for the sheet to develop a noticeable discoloration and/or embrittlement, indicating deterioration due to oxidation in the presence of ultraviolet light.

This test was repeated for a total of seven stabilizers in accordance with the invention, having the formulae indicated in Table I. The following results were obtained:

TABLE I

| Ex. No. | Stabilizer | Hours to Failure |
|---|---|---|
| Control | 2,2,6,6-tetramethylpiperidinyl-4-benzoate | 270 |
| 1 | [structure] | 390 |
| 2 | [structure] | 420 |
| 3 | [structure] | 420 |
| 4 | [structure] | 480 |
| 5 | [structure] | 370 |
| 6 | [structure] | 460 |
| 7 | [structure] | 450 |

It is apparent that each of the seven stabilizers in accordance with the invention is far superior to the control, a conventional ultraviolet light stabilizer for polyvinyl chloride, 2,2,6,6-tetramethyl-piperidyl-4-benzoate.

EXAMPLES 8 to 16

Polypropylene compositions were prepared, using nine stabilizers of the invention and three of the prior art, and having the following formulation:

| Ingredient | Parts by Weight |
|---|---|
| Polypropylene | 100 |
| Distearylthiodipropionate | 0.3 |
| Irganox 1076[1] | 0.1 |
| Stabilizer as shown in Table II | 0.3 |

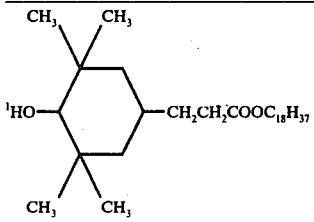

The composition was thoroughly blended in a Brabender Plastograph, and then compression-molded to form sheets 0.5 mm thick. Pieces 2.5 cm square were cut off from the sheets and exposed to a carbon arc in a Weather-O-Meter for 350 hours. Elongation before and after 350 hours exposure was determined, and the percent of retention of elongation is shown in Table II.

TABLE II

| Ex. No. | Stablizer | % Elongation Retention |
|---|---|---|
| Control 1 | 2(2'-hydroxy-5'-methylphenyl)benzotriazole | 17.5 |
| Control 2 | 2,2,6,6-tetramethylpiperidinyl-4-benzoate | 4.7 |
| Control 3 | bis(2,2,6,6-tetramethyl-4-piperidinyl)sebacate | 5.3 |
| 8 | | 39.5 |
| 9 | | 42.7 |
| 10 | | 43.6 |
| 11 | | 43.2 |

TABLE II-continued

| Ex. No. | Stablizer | % Elongation Retention |
|---|---|---|
| 12 | (structure) | 49.5 |
| 13 | (structure) | 41.4 |
| 14 | (structure) | 53.2 |
| 15 | (structure) | 50.1 |
| 16 | (structure) | 52.0 |

TABLE II-continued

| Ex. No. | Stablizer | % Elongation Retention |
|---|---|---|
| | (X : t-butyl) | |

It is apparent from the above results that the compounds of the invention are superior stabilizers in enhancing the resistance of the polypropylene polymer composition to deterioration in the presence of ultraviolet light.

EXAMPLES 17 to 23

Seven ethylene-vinyl acetate copolymer compositions were prepared using six stabilizers of the invention and one of the prior art, and having the following formulation:

| Ingredient | Parts by Weight |
|---|---|
| Ethylene-vinylacetate copolymer | 100 |
| Stabilizer as shown in Table III | 0.2 |

The stabilizer was blended with the polymer on a two-roll mill at 120° C, and sheets 1 mm thick were then compression molded at 120° C from the resulting blend. Pieces 2.5 cm square were cut off from the sheets and exposed to ultraviolet light in a Weather-O-Meter for 500 hours. At the start and at the conclusion of the test, the tensile strength of the sheet samples was determined. The results are given in Table III as % retention of the initially determined tensile strength:

TABLE III

| Ex. No. | Stabilizer | % Retention of Tensile Strength |
|---|---|---|
| Control | 2-hydroxy-4-methoxybenzophenone | 71 |
| 17 | [structure] | 85 |
| 18 | [structure] | 84 |
| 19 | [structure] | 83 |
| 20 | [structure] | 80 |
| 21 | [structure] | 79 |

TABLE III-continued

| Ex. No. | Stabilizer | % Retention of Tensile Strength |
|---|---|---|
| 22 | [structure with piperidinyl, phosphite, bisphenol groups] | 82 |
| 23 | [structure with piperidinyl, phosphite, cyclohexane diol groups] | 80 |

It is apparent from the results that the stabilizer compositions in accordance with the invention are superior to 2-hydroxy-4-methoxybenzophenone in enhancing the resistance of the ethylene-vinyl acetate copolymer to deterioration in the presence of ultraviolet light.

EXAMPLES 24 to 31

Seven high density polyethylene compositions were prepared using five stabilizers of the invention and two of the prior art, and having the following formulation:

| Ingredient | Parts by Weight |
|---|---|
| High-density polyethylene | 100 |
| Stabilizer as shown in Table IV | 0.1 |

The stabilizer was blended with the polymer on a two-roll mill and sheets 0.5 mm thick were prepared by compression molding of the blend. Pieces 2.5 cm square were cut off from the sheets, and exposed in a Weather-O-Meter to ultraviolet light. The time in hours when degradation set in, as determined by a significant discoloration and/or embrittlement, was noted as hours to failure, and the results are reported in Table IV:

TABLE IV

| Ex. No. | Stabilizer | Hours to Failure |
|---|---|---|
| Control | 2,2,6,6-tetramethylpiperidinyl-4-benzoate | 730 |
| 24 | $HOC_{10}H_{20}O-P-O-$[piperidinyl NH] structure with HO | 1350 |
| 25 | [bisphenol-phosphite-piperidinyl structure]$_2$ | 1420 |
| 26 | [C$_{18}$H$_{37}$O, piperidinyl, phosphite, bisphenol structure] | 1400 |
| 27 | [C$_{18}$H$_{37}$O, piperidinyl, diphosphite, C$_6$H$_{12}$ structure] | 1450 |

TABLE IV-continued

| Ex. No. | Stabilizer | Hours to Failure |
|---|---|---|
| 28 | [structure] | 1320 |
| 29 | [structure] | 1430 |
| 30 | [structure] | 1460 |
| 31 | [structure] | 1420 |

The stabilizers of the invention are clearly superior to the control in enhancing resistance of the polyethylene to degradation under ultraviolet light.

EXAMPLES 32 to 37

Six acrylonitrile-butadiene-styrene terpolymer resin compositions were prepared using six stabilizers of the invention and compared to one of the prior art, all seven having the following formulation:

| Ingredient | Parts by Weight |
|---|---|
| Acrylonitrile-butadiene-styrene terpolymer | 100 |
| Stabilizer as shown in Table V | 0.1 |

The stabilizer was blended with the resin on a two-roll mill, and sheets 3 mm thick were prepared by compression molding of the resulting blend. Pieces 2.5 cm square were cut off from the sheets, and subjected to ultraviolet light in a Weather-O-Meter for 800 hours. Tensile strength before and after the test exposure was determined, and the results reported as the percent of tensile strength retained, at the end of this time, in Table V.

TABLE V

| Ex. No. | Stabilizer | % Retention of Tensile Strength |
|---|---|---|
| Control | 2-hydroxy-4-octoxybenzophenone | 75 |
| 32 | [structure] | 88 |

TABLE V-continued

| Ex. No. | Stabilizer | % Retention of Tensile Strength |
|---|---|---|
| 33 | 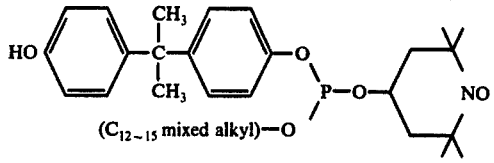 | 92 |
| 34 | 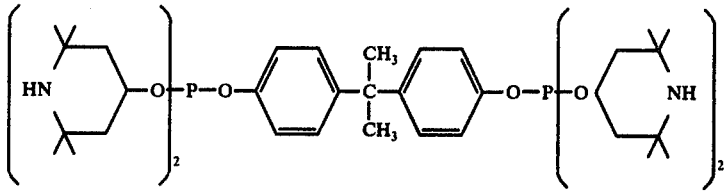 | 94 |
| 35 | 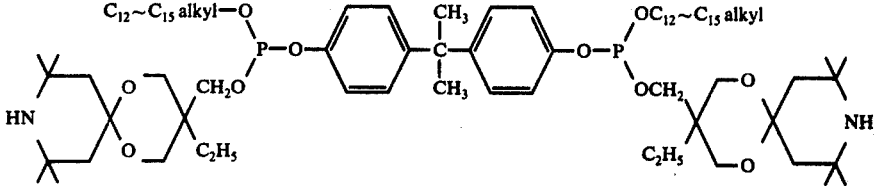 | 91 |
| 36 | 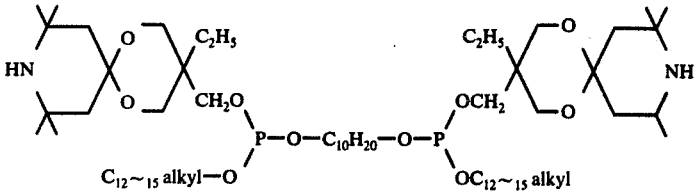 | 89 |
| 37 | 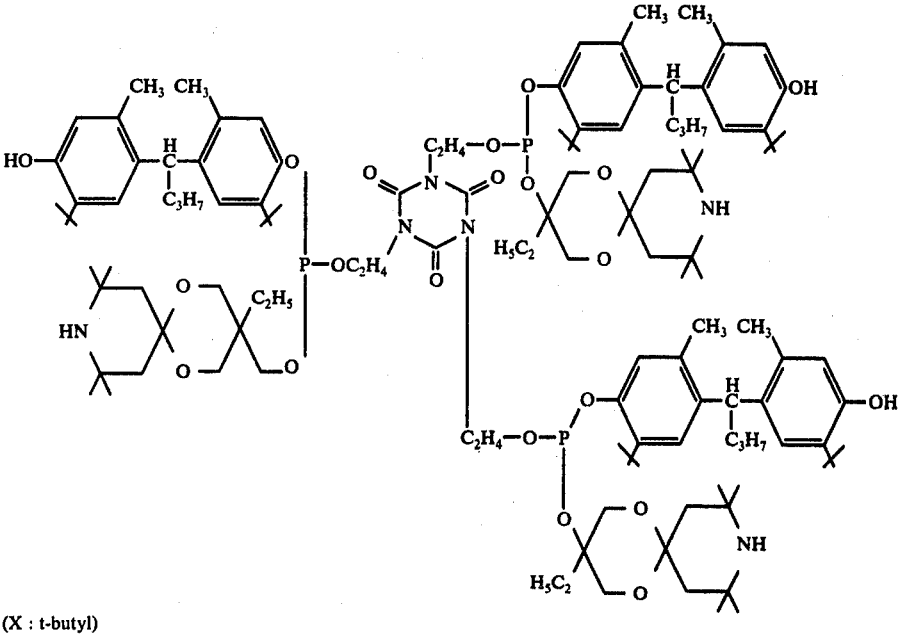 | 93 |

(X : t-butyl)

The stabilizers of the invention are clearly superior to the control in enhancing resistance of the acrylonitrile-butadiene-styrene terpolymer to degradation under ultraviolet light.

EXAMPLES 38 to 44

Seven polyamide resin compositions were prepared using seven stabilizers of the invention, all having the following formulation:

| Ingredient | Parts by Weight |
|---|---|
| Poly-epsilon-caprolactam | 100 |

-continued

| Ingredient | Parts by Weight |
|---|---|
| Stabilizer as shown in Table VI | 0.1 |

The stabilizer was blended with the finely powdered polyepsilon-caprolactam in a ball mill for fifteen minutes, and the resulting powder was then compression-molded at 250° C to form sheets 0.5 mm thick. Pieces 2.5 cm square were cut out from the sheets, and exposed to ultraviolet light in a Weather-O-Meter for 120 hours. At the conclusion of the test period, the color of the sheets was noted. The change in color is given in Table VI.

TABLE VI

| Ex. No. | Stabilizer | Change in Color |
|---|---|---|
| Control | None | yellow |
| 38 | $HOC_6H_{12}O-P$ [structure] | none |
| 39 | [structure] | none |
| 40 | [structure] | none |
| 41 | [structure] | none |
| 42 | [structure] | none |
| 43 | [structure] | none |

TABLE VI-continued

| Ex. No. | Stabilizer | Change in Color |
|---|---|---|
| 44 | [structure: bis(2,2,6,6-tetramethylpiperidyl spiro-dioxaphosphite) linked via O-aryl-CH(C₃H₇)-aryl-O with CH₃ substituents] | none |

The stabilizers of the invention are clearly superior to the control in enhancing resistance of the poly-episilon-caprolactam to degradation under ultraviolet light.

EXAMPLES 45 to 51

Seven rubber-modified polystyrene resin formulations were prepared having the following composition:

The compositions were extruded to form pellets, and then test pieces were molded from the pellets by injection molding at 230° C. The test pieces were irradiated with ultraviolet light for 320 hours in a Weather-O-Meter. Tensile strength before and after exposure was determined, and the percent tensile strength retained after the exposure is given in Table VII:

TABLE VII

| Example No. | Stabilizer | % Retention of Tensile Strength |
|---|---|---|
| Control | 2-hydroxy-4-octoxybenzophenone | 50.1 |
| 45 | [structure with HN-piperidyl-O-P(-O-aryl-C(CH₃)₂-aryl-O-)-O-piperidyl-NH] | 73.1 |
| 46 | [structure with spiro dioxa groups, C₂H₅, CH₂O, P-O-aryl(CH₃)-CH(C₃H₇)-aryl(CH₃)-O-P, cyclohexyl-phenyl O groups] | 77.2 |
| 47 | [structure with C₁₈H₃₇O-P, cyclohexyl-C(CH₃)₂-cyclohexyl, spiro dioxa with C₂H₅] | 75.6 |
| 48 | [structure with spiro bis-dioxa CH₂-O groups, P-O-cyclohexyl-C(CH₃)₂-cyclohexyl-O-P] | 70.3 |

| Ingredient | Parts by Weight |
|---|---|
| Rubber modified polystyrene | 100 |
| Ca-stearate | 1.0 |
| Stabilizer as shown in Table VII | 0.25 |

Having regard to the foregoing disclosure, the following is claimed as the inventive and patentable embodiments thereof:

1. 2,2,6,6-tetramethyl-piperidyl-4-phosphites having the formula:

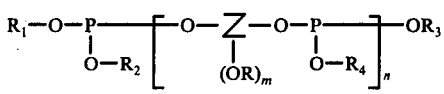

wherein:

$R_1$ is selected from the group consisting of:

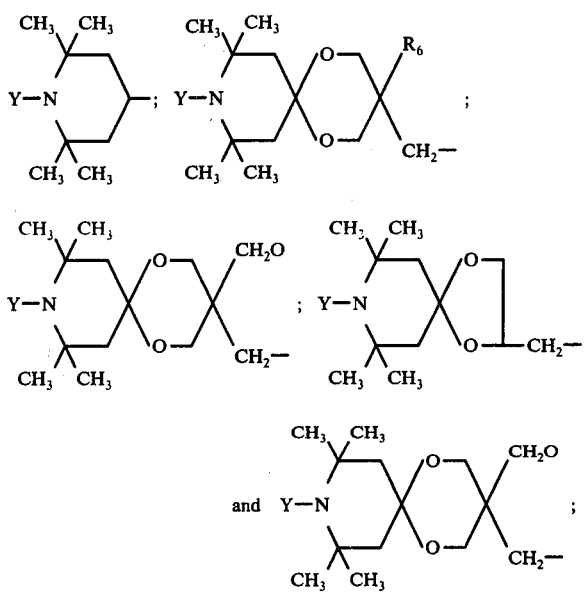

$R_2$, $R_3$ and $R_4$ are selected from the group consisting of:

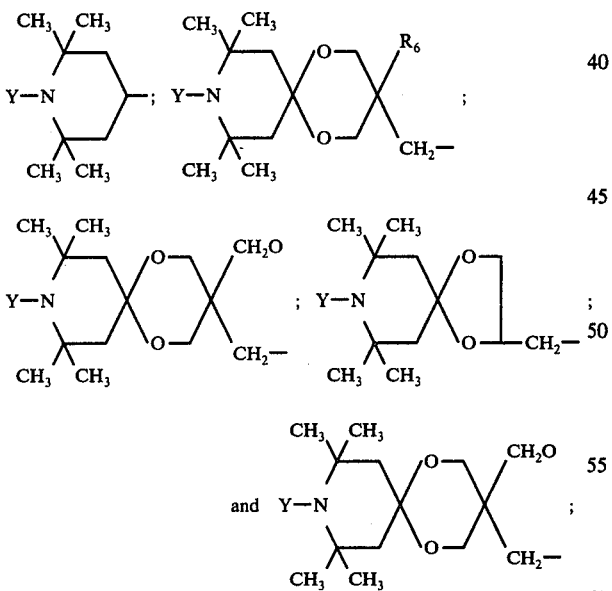

hydrogen, alkyl having from 1 to about 20 carbon atoms; aryl and hydroxylaryl having from 6 to about 20 carbon atoms; alkyl aryl and aryl alkyl having from 7 to about 20 carbon atoms; hydroxyalkyl and hydroxyalkylene oxyalkylene having from 2 to about 30 carbon atoms; and $R_1$ and $R_2$; and $R_3$ and $R_4$; taken together to form

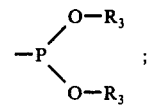

R is selected from the group consisting of hydrogen and

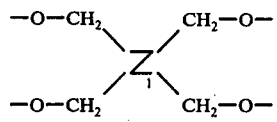

$R_6$ is alkyl having from 1 to about 6 carbon atoms;
Y is selected from the group consisting of hydrogen and oxygen;
$m$ is a number selected from 0, 1, 2, 3 and 4;
$n$ is a number selected from zero to 20, when $n$ is zero, at least one of $R_2$ and $R_3$ being derived from a polyol or a polyphenol; and
Z is selected from the group consisting of bivalent, trivalent and tetravalent alkylene having from 2 to about 30 carbon atoms; bivalent, trivalent and tetravalent arylene, bis arylene and tris, arylene, having from 6 to about 30 carbon atoms; mono, di or tri N-substituted cyanuric acid; and taken with OR, $R_1$ or $R_2$ and $R_3$ or $R_4$ to form the group:

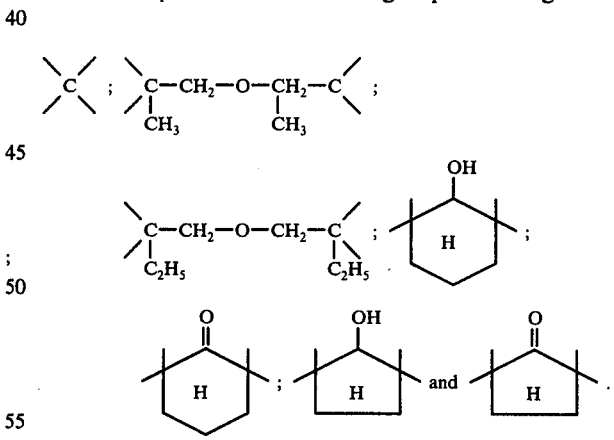

in which $Z_1$ is selected from the group consisting of 2. 2,2,6,6-tetramethyl-piperidyl-4-phosphites according to claim 1, in which the Z substituent is alkylene derived from a polyol and the compounds have the formula:

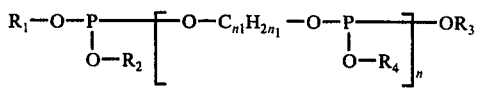

where:

$n_1$ is a number from 2 to 20; and $R_1$, $R_2$, $R_3$, $R_4$ and n are as in claim 1.

3. 2,2,6,6-tetramethyl-piperidyl-4-phosphites according to claim 1, in which Z is arylene, derived from a polyphenol residue, and the compounds have the formula:

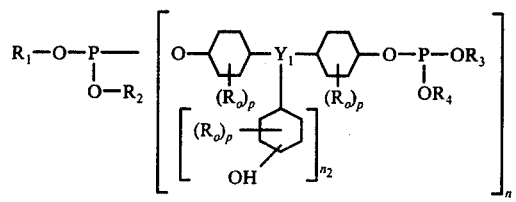

where:
$R_0$ is alkyl having from one to about twenty carbon atoms;
p is a number selected from zero to 4;
$n_2$ is zero or 1; and
$Y_1$ is a bivalent or trivalent linking radical and is selected from the group consisting of alkylene groups having from one to about twenty carbon atoms; oxygen; sulfur; cycloalkylene having from about five to about seven carbon atoms; and arylene having from six to about thirty atoms.
$R_1$, $R_2$, $R_3$, $R_4$, and n are as in claim 1.

4. 2,2,6,6-tetramethyl-piperidyl-4-phosphites according to claim 1 in which Z is taken together with OR, $R_1$ or $R_2$ and $R_3$ or $R_4$, and the compounds have the formula:

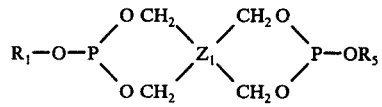

where $R_1$, $R_5$ and $Z_1$ are as in claim 1.

5. A compound according to claim 1 in which m is zero.

6. A compound according to claim 2 in which m is 1 and R is hydrogen.

7. A compound according to claim 2 in which m is 1 and R is

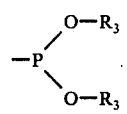

8. A compound according to claim 1 in which $R_1$ is

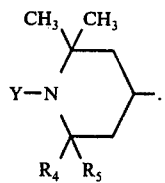

9. A compound according to claim 1 in which $R_1$ is

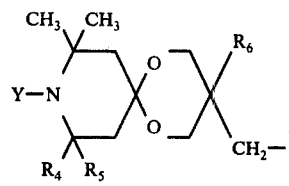

10. A compound according to claim 1 in which $R_1$ is

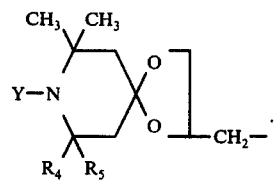

11. A compound according to claim 1 in which $R_1$ is

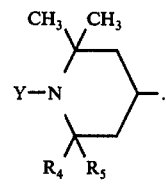

12. A compound according to claim 1 in which Z is alkylene.

13. A compound according to claim 1 in which Z is arylene.

14. A compound according to claim 1 in which Y is hydrogen.

15. A compound according to claim 1 in which Y is oxygen.

16. A compound according to claim 1 in which n is one.

17. A compound according to claim 1 having the formula:

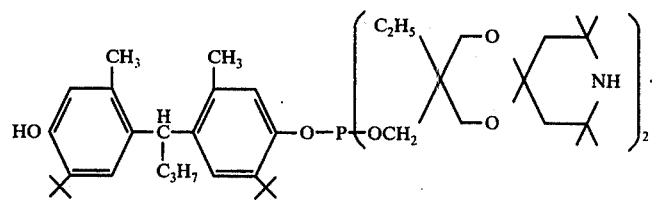

18. A compound according to claim 1 having the formula:

19. A compound according to claim 1 having the formula:

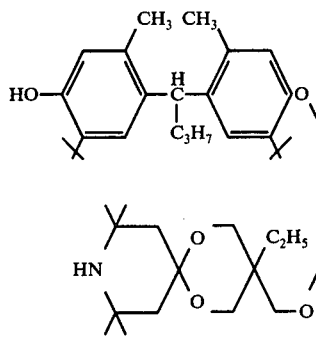 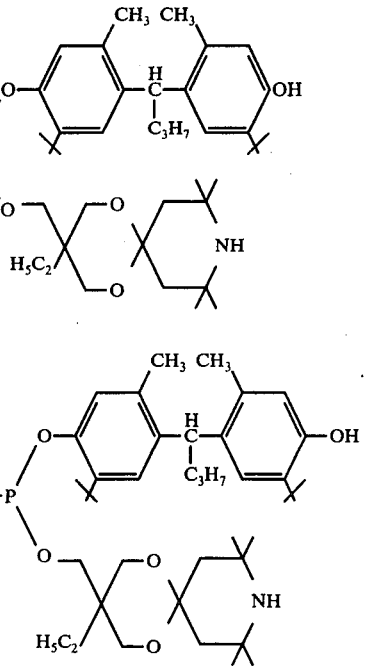

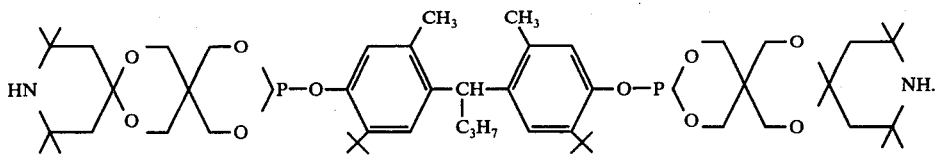

20. A compound according to claim 1 having the formula:

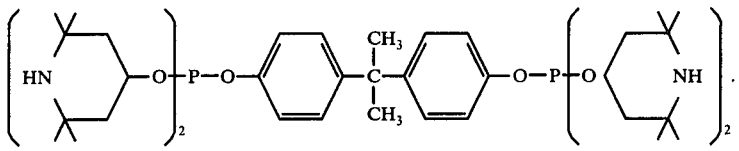

21. A polyvinyl chloride resin composition having improved resistance to deterioration when heated at 350° F, comprising a polyvinyl chloride resin formed at least in part of the recurring group

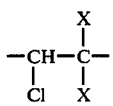

and having a chlorine content in excess of 40 percent, where X is either hydrogen or chlorine; and an amount to improve resistance to deterioration of the resin of a compound in accordance with claim 1.

22. a polyvinyl chloride resin composition in accordance with claim 21, in which the polyvinyl chloride resin is polyvinyl chloride homopolymer.

23. A polyvinyl chloride resin composition in accordance with claim 21, in which the polyvinyl chloride resin is a copolymer of vinyl chloride and vinyl acetate.

24. An olefin polymer composition having improved resistance to deterioration comprising an olefin polymer selected from the group consisting of polymers of alpha-olefins having from two to six carbon atoms and polystyrene, and an amount of improve resistance to deterioration of the resin of a compound in accordance with claim 1.

25. An olefin polymer composition in accordance with claim 24 wherein the polyolefin is polypropylene.

26. An olefin polymer composition in accordance with claim 24 wherein the polyolefin is polyethylene.

27. An acrylonitrile-butadiene-styrene polymer having improved resistance to deterioration when heated at 300° F and above and an amount to improve resistance to deterioration of the resin of a compound in accordance with claim 1.

28. A synthetic rubbery diene polymer composition having improved resistance to deterioration comprising a rubbery diene polymer and an amount to improve resistance to deterioration of the resin of a compound in accordance with claim 1.

29. A polyamide resin composition having improved resistance to deterioration comprising a polyamide resin and an amount to improve resistance to deterioration of the resin of a compound in accordance with claim 1.

30. An ethylene-vinyl acetate copolymer composition having improved resistance to deterioration comprising an ethylene-vinyl acetate copolymer and an amount to improve resistance to deterioration of the resin of a compound in accordance with claim 1.

* * * * *

UNITED STATES PATENT OFFICE
CERTIFICATE OF CORRECTION

Patent No. 4,096,114                     Dated June 20, 1978

Inventor(s) Motonobu Minagawa et al

It is certified that error appears in the above-identified patent and that said Letters Patent are hereby corrected as shown below:

| | | |
|---|---|---|
| [30] | : | "50-9929" should be --50 99291-- |
| Column 2, line 41 | : | "wherein" should be --when-- |
| Column 8, line 68 | : | insert --and $R_3$ and $R_4$-- after "$R_2$" |
| Column 9, line 68 | : | insert --$R_4$-- after "$R_3$" |
| Column 10, line 27 | : | insert --carbon-- after "seven" |
| line 28 | : | insert --carbon-- after "thirty" |
| line 56 | : | "napthyl" should be --naphthyl-- |
| Column 11, lines 17-18 | : | "cyc-balkylene" should be --cyc-loalkylene-- |

Column 12, line 20 :

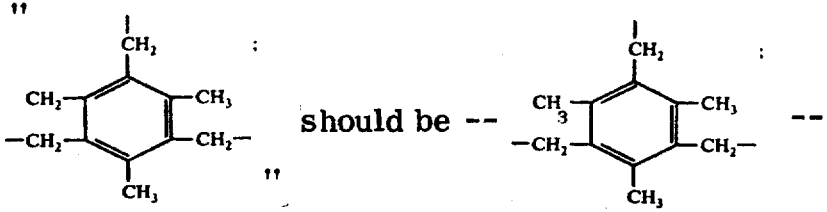

line 46 : "─(S)x─ where X" should be ── ─ $(S)_x$ ─ where x ── line 55 :

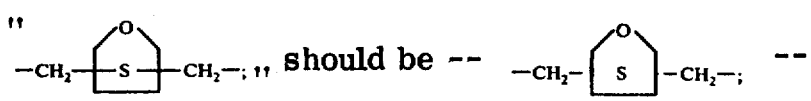

UNITED STATES PATENT OFFICE
CERTIFICATE OF CORRECTION

Patent No. 4,096,114　　　　　Dated June 20, 1978

Inventor(s) Motonobu Minagawa et al

It is certified that error appears in the above-identified patent and that said Letters Patent are hereby corrected as shown below:

Column 12, line 58 :

line 61 : 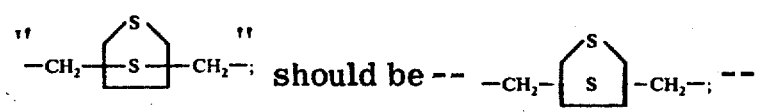

Column 14 : The reference to [1] at line 15 is missing from the bottom of the page. Add
-- [1] It will be understood that  represents 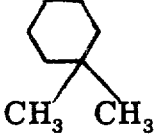
and  represents 
t-$C_4H_9$ --

Column 15 : Move "No. 14" from bottom of page to top of column 17.

UNITED STATES PATENT OFFICE
CERTIFICATE OF CORRECTION

Patent No. 4,096,114     Dated June 20, 1978

Inventor(s) Motonobu Minagawa et al

It is certified that error appears in the above-identified patent and that said Letters Patent are hereby corrected as shown below:

Column 17, Formula 20 :

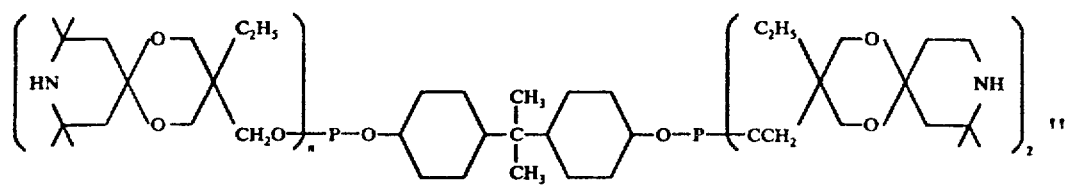

should be

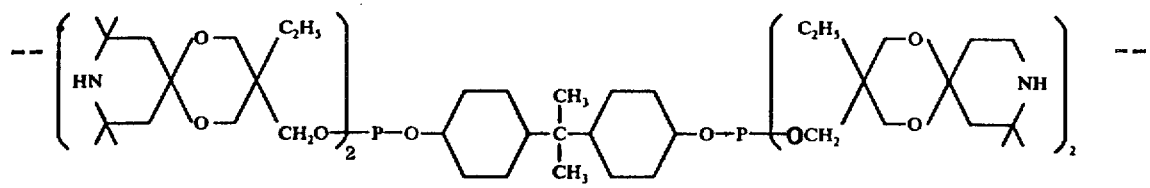

Column 19, Formula 21 :

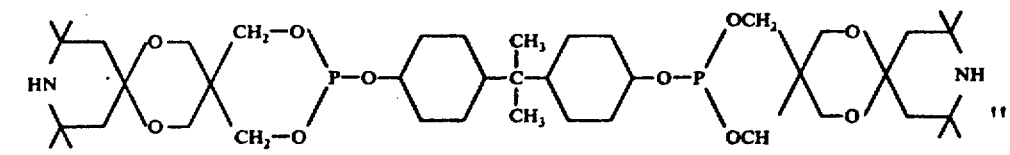

should be

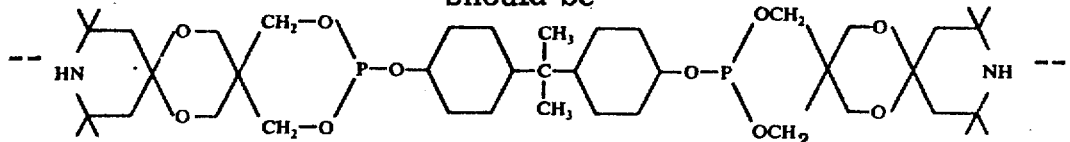

UNITED STATES PATENT OFFICE
CERTIFICATE OF CORRECTION

Patent No. 4,096,114    Dated June 20, 1978

Inventor(s) Motonobu Minagawa et al

It is certified that error appears in the above-identified patent and that said Letters Patent are hereby corrected as shown below:

Column 19, Formula 25 :

" No. 25

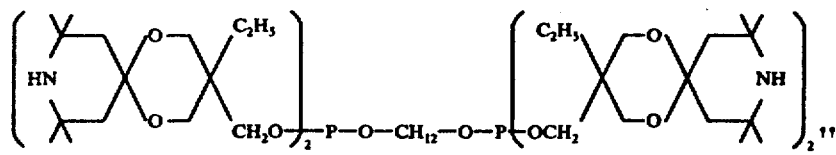

should be

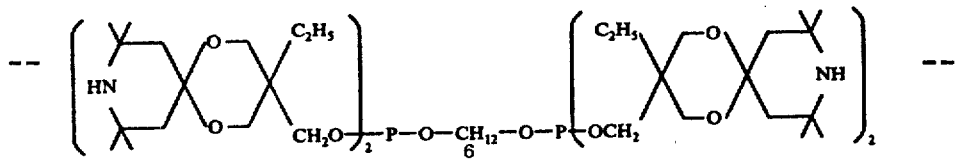

Column 19, Formula 27 :

" No. 27

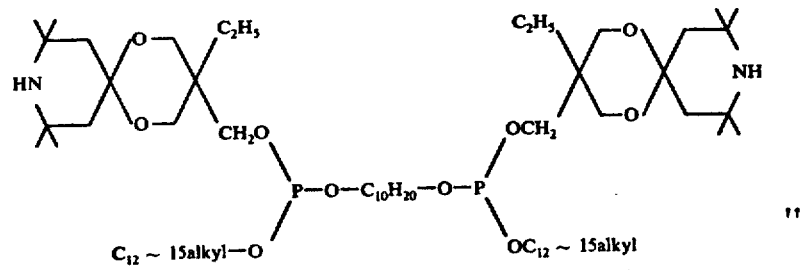

should be

UNITED STATES PATENT OFFICE
CERTIFICATE OF CORRECTION

Patent No. 4,096,114   Dated June 20, 1978

Inventor(s) Motonobu Minagawa et al

It is certified that error appears in the above-identified patent and that said Letters Patent are hereby corrected as shown below:

No. 27

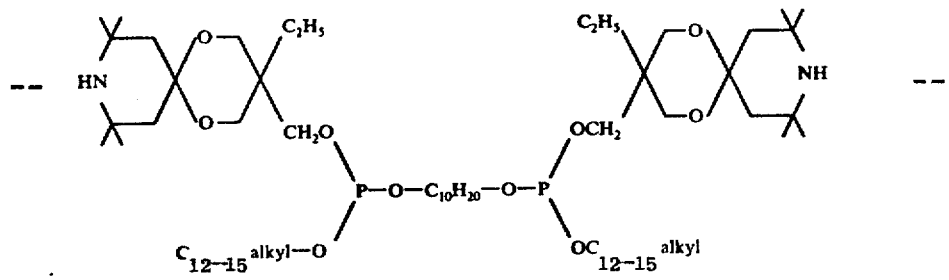

Column 19   : Move "No. 29" from bottom of page to top of column 21.

Column 21   : Move "No. 36" from bottom of page to top of column 23.

Column 23, Formula 36 :

"
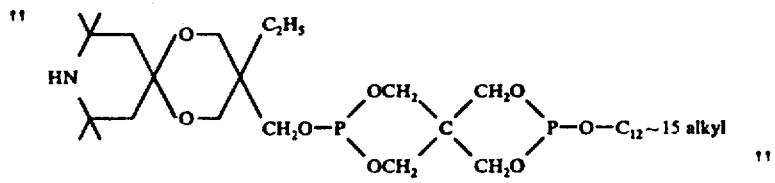
"

should be

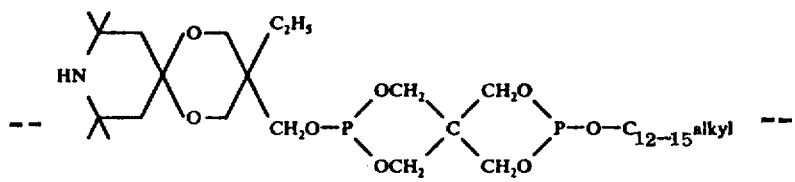

UNITED STATES PATENT OFFICE
CERTIFICATE OF CORRECTION

Patent No. 4,096,114  Dated June 20, 1978

Inventor(s) Motonobu Minagawa et al

It is certified that error appears in the above-identified patent and that said Letters Patent are hereby corrected as shown below:

Column 23 : Move "No. 43" from bottom of page to top of column 25.

Column 27, line 2 : "dioxaspyrao" should be --dioxaspyro-- line 25 : insert -ethyl-3 -- before "hydroxymethyl"

line 58 : "ethylenepentane" should be --ethylenepentene--

Column 29, Formula 4 :

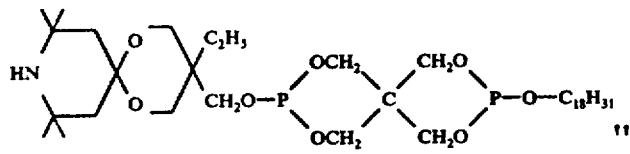

should be

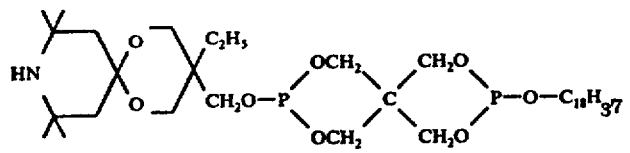

Column 32, line 5 : Insert reference -- 1 -- before formula and delete "1" before "HO"

line 17 : "are" should be --arc--

UNITED STATES PATENT OFFICE
CERTIFICATE OF CORRECTION

Patent No. 4,096,114  Dated June 20, 1978

Inventor(s) Motonobu Minagawa et al

It is certified that error appears in the above-identified patent and that said Letters Patent are hereby corrected as shown below:

Column 35, Formula 20 :

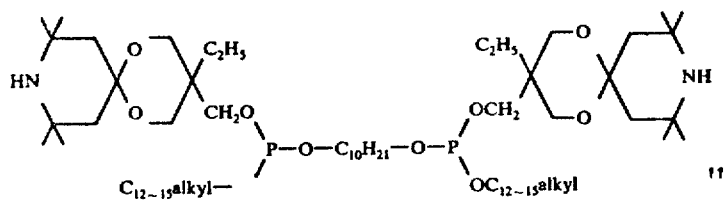

should be

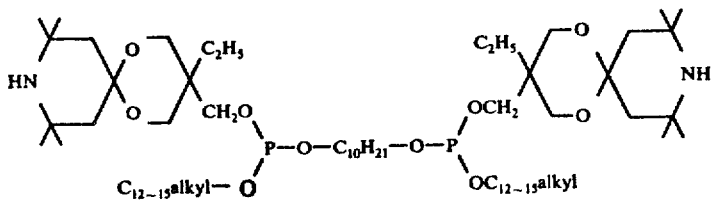

Column 47, line 61 : "hydroxylaryl" should be --hydroxyaryl--

Column 52, line 30 : "of" should be --to--

Signed and Sealed this

Twenty-third Day of October 1979

[SEAL]

Attest:

RUTH C. MASON  
Attesting Officer

LUTRELLE F. PARKER  
Acting Commissioner of Patents and Trademarks